United States Patent [19]

Frazer

[11] Patent Number: Plant 6,856

[45] Date of Patent: Jun. 13, 1989

[54] DIEFFENBACHIA HYBRIDA TORCH

[75] Inventor: Edwin J. Frazer, Brisbane, Australia

[73] Assignee: Hartman Plant Laboratories, Inc., Santa Paula, Calif.

[21] Appl. No.: 23,605

[22] Filed: Mar. 9, 1987

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Hale and Dorr

[57] ABSTRACT

A new and distinct cultivar of Dieffenbachia known as Dieffenbachia Hybrida Torch, which is a seedling cross between Seguine Lineata and an unnamed seedling of a cross between Dieffenbachia Marianne and Exotica.

1 Drawing Sheet

The invention comprises a new and distinct cultivar of Dieffenbachia known as Dieffenbachia Hybrida Torch.

The new cultivar is a product of a seedling cross between Dieffenbachia Seguine Lineata and an unnamed seedling of a cross between Dieffenbachia Marianne and Exotica.

The following observations, measurements and values describe plants grown in Alva, Fla. under greenhouse conditions that closely approximate those generally used in horticultural practice. All color references are measured against The Royal Horticultural Society colour chart. Colors are approximate as color depends on horticultural practices such as light level and fertilization rate among others.

The following traits have been repeatedly observed to be characteristics which in combination distinguish Dieffenbachia Torch from other commercially available Dieffenbachia.

DISTINCTIONS

1. The leaves are available in their variegation pattern.
2. Older leaves become greener with age.
3. The intenode distance is great and the internode color is dark and shiny.
4. The petioles are white with green stripes.
5. The petioles do not clasp the stem so the combination of white petioles and green stem gives great contrast.
6. Breaks are widely spaced so stem characteristics can be seen.
7. The main stem is decumbent.
8. The midrib is flexible enough to enable touching the tip of the leaf to its base without damage.
9. Continues to grow at 50° F.

The appearance and distinctive character of Torch is shown in the FIGURE which is a true color photograph of the cultivar in an eight-inch pot.

DESCRIPTION

Propagation: Asexual production either through tissue culture or division.

Plant: In a 6 inch pot, Torch will be approximately 25 cm to 29 cm from the soil surface to the junction of the petioles of the last two unrolled leaves and approximately 54 cm to 58 cm in width after aproximately 26 weeks to 36 weeks under appropriate growing conditions from tissue culture. All measurements are based on the above parameters.

Stem:

*Growth pattern.*—The stem is slightly decumbent in growth and will be approximately 2.0 cm to 2.5 cm in diameter 5 cm above the soil surface. Internode distance will be approximately 2.1 cm to 2.5 cm at a height of 3 cm above the soil.

*Color.*—The stem is dark green.

Petiole (based on the fourth expanded leaf from apex of the main shoot):

*Pattern.*—The petiole has fleshy edges extending from the midrib that will be referred to as wings. The wings will be approximately 5 mm to 7 mm wide 1 cm below the leaf base. The wings extend from the base of the petiole to within approximately 1.6 cm to 2.0 cm of the leaf base. The apex of the wings is emarginate. The petiole follows the stem axis but diverges from the axis approximately 5.8 cm to 6.4 cm from the leaf base forming a horizontal distance from the edge of the stem to the leaf base of approximately 2.0 cm to 2.4 cm.

*Physical dimensions.*—The petiole will be approximately 11.3 cm to 12.0 cm from its base to the base of the leaf. The petiole will be approximately 5 mm to 7 mm in diameter one-half way between the top of the wing to the bottom of the leaf.

*Color and color pattern.*—The petiole wings will be white with green stripes and the midrib will be the same.

Leaf:

*Growth pattern.*—The leaf will be ovate with a aristate/cuspidate apex and a cordate base. The margin is entire. The leaf is asymmetric with the side of the leaf unrolling first having less surface area and less undulations on the leaf margin than the side unrolling last. The leaf is oriented 20° to the stem axis at the time of full unrolling changing to 90° to the stem axis as more leaves unroll above it. The midrib droops slightly over the length of the leaf. The leaf blade is flat from the midrib to the margin.

*Physical dimensions.*—For the potsize and growing time indicated, the largest leaf will be approximately 25 cm to 29 cm long and approximately 13 cm to 15 cm wide. An average sized leaf will be approximately 20 cm to 23 cm long and approximately 8 cm to 10 cm wide. The leaf thickness is medium.

*Midrib.*—The midrib is thick and white with green blotches.

*Primary veins.*—The primary veins are sunken into the adaxial side and protruding out of the abaxial side.

*Color and pattern.*—The adaxial surface of the mature, older leaf has a midrib color of 138B, and a leaf blade background color of 145A, blotched with irregular areas of 136A. The abaxial surface of the mature, older leaf has a midrib color of 146B at the basal-surface, changing to grayer than 137A at the surface where the leaf blade is attached thereto; the leaf blade background color is grayer than 137A, blotched with yellower and lighter than 139D. The adaxial surface of the newly-opened leaf has a midrib color of 145D, striped with 139A and a leaf blade color of 1C, blotched with irregular spots of 139A. The petiole wings are a white that is greener than 157C with green stripes of 138A. The abaxial surface of the newly-opened leaf has a midrib color of 145B and a leaf blade background color that is greener than 157C, blotched with patches of 137C.

*Texture.*—The leaf appears ribbed with a dull finish.

Axillary breaks: There will be approximately 5 to 7 axillary breaks with at least 1 leaf expanded. Leaves will show color by the second leaf and will have true color and pattern by the fourth leaf.

Inflorescences: not present.

Roots: Thick white roots with finer laterals.

General observations: Diffenbachia Torch is a tall long-leaved variety that has highly variegated green and white leaves. The pattern is irregular and becomes greener overall as the leaves age. The striped petioles provide good contrast to the darker leaves at the base of the plant. The decumbent stem gives the plant greater width. The plant habit is open exposing the dark stem and white petioles. This variety will actively grow at 50° F.

I claim:

1. A new and distinct cultivar of Dieffenbachia as described and illustrated.

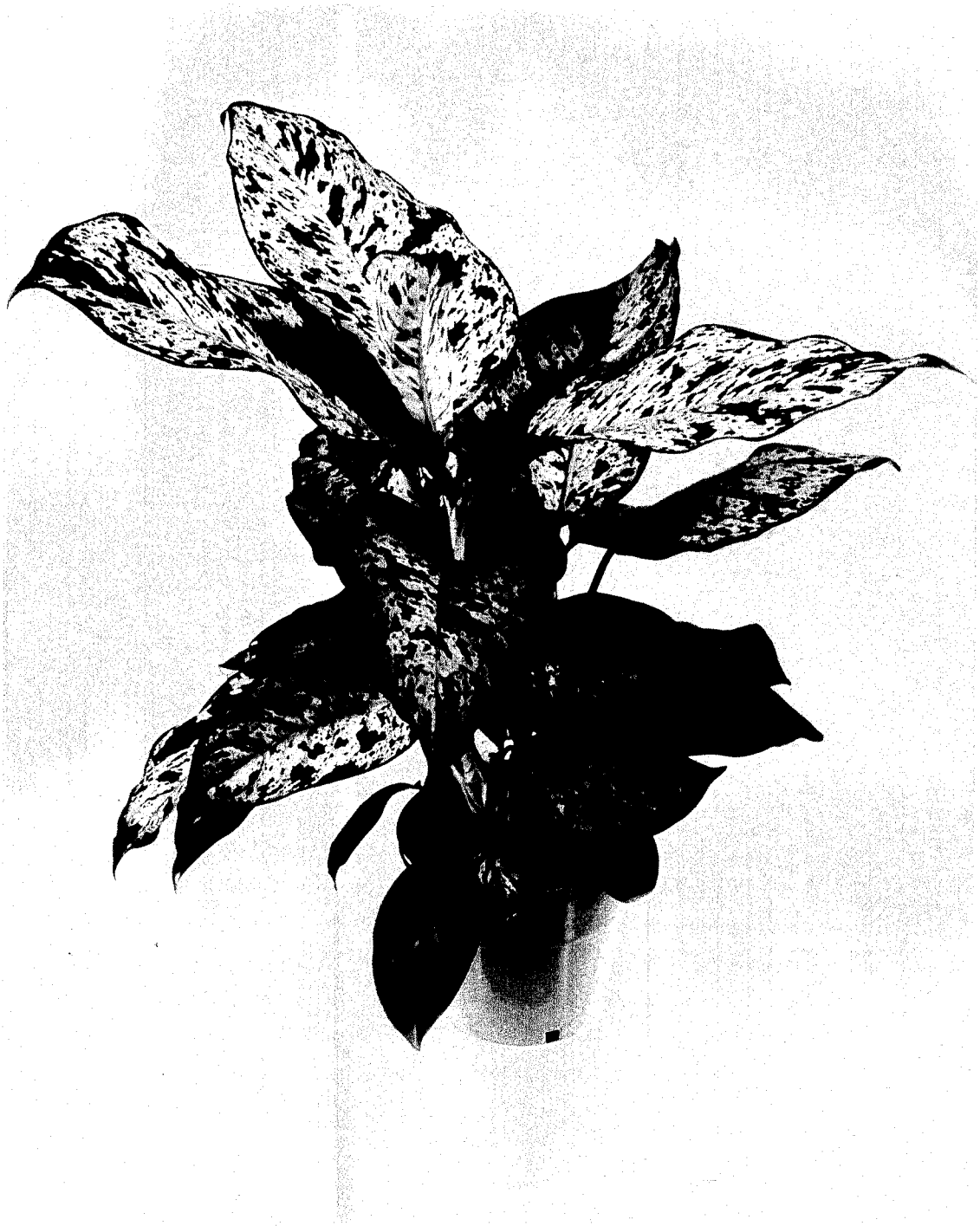

* * * * *